United States Patent
Gildert

(10) Patent No.: US 6,187,980 B1
(45) Date of Patent: Feb. 13, 2001

(54) HYDROGENATION OF BENZENE TO CYCLOHEXANE

(75) Inventor: Gary R. Gildert, Houston, TX (US)

(73) Assignee: Catalytic Distillation Technologies (*) Notice: Under 35 U.S.C. 154(b), the term of this patent shall be extended for 0 days.

(21) Appl. No.: 09/408,358

(22) Filed: Sep. 29, 1999

(51) Int. Cl.[7] .............................. C07C 5/10; C10G 45/54
(52) U.S. Cl. ..................... 585/266; 208/144; 203/DIG. 6
(58) Field of Search ........................... 585/266; 208/143, 208/144; 203/DIG. 6; 202/29

(56) References Cited

U.S. PATENT DOCUMENTS

| 2,373,501 | 4/1945 | Peterson . |
| 4,079,092 | 3/1978 | Hayes et al. . |
| 4,087,353 | 5/1978 | Rausch . |
| 4,098,683 | 7/1978 | Conway . |
| 4,225,418 | 9/1980 | Hilfman . |
| 4,240,900 | 12/1980 | Gilbert et al. . |
| 4,857,666 | 8/1989 | Barger et al. . |
| 5,368,691 | * 11/1994 | Asselineau et al. ................. 203/29 |
| 5,599,997 | 2/1997 | Hearn et al. . |
| 5,773,670 | 6/1998 | Gildert et al. . |
| 5,856,602 | 1/1999 | Gildert et al. . |
| 6,072,091 | * 6/2000 | Cosyns et al. ..................... 585/259 |
| 6,100,435 | * 8/2000 | Silverberg et al. ................. 585/318 |

* cited by examiner

Primary Examiner—Bekir L. Yildirim
(74) Attorney, Agent, or Firm—Kenneth H. Johnson

(57) ABSTRACT

A process for the production of cyclohexane by the hydrogenation of benzene is provided wherein the reactor is operated at a pressure wherein the reaction mixture is boiling under low hydrogen partial pressure in the range of about 0.1 psia to less than 200 psia at 0 to 350 psig overhead pressure. The catalyst is provided as a catalytic distillation structure such that the reaction is concurrently occurring with a distillation. The benzene is fed at a point above the bed and the hydrogen is fed below the bed. All of the overheads may be returned as reflux to provide cooling within the catalyst bed.

10 Claims, 1 Drawing Sheet

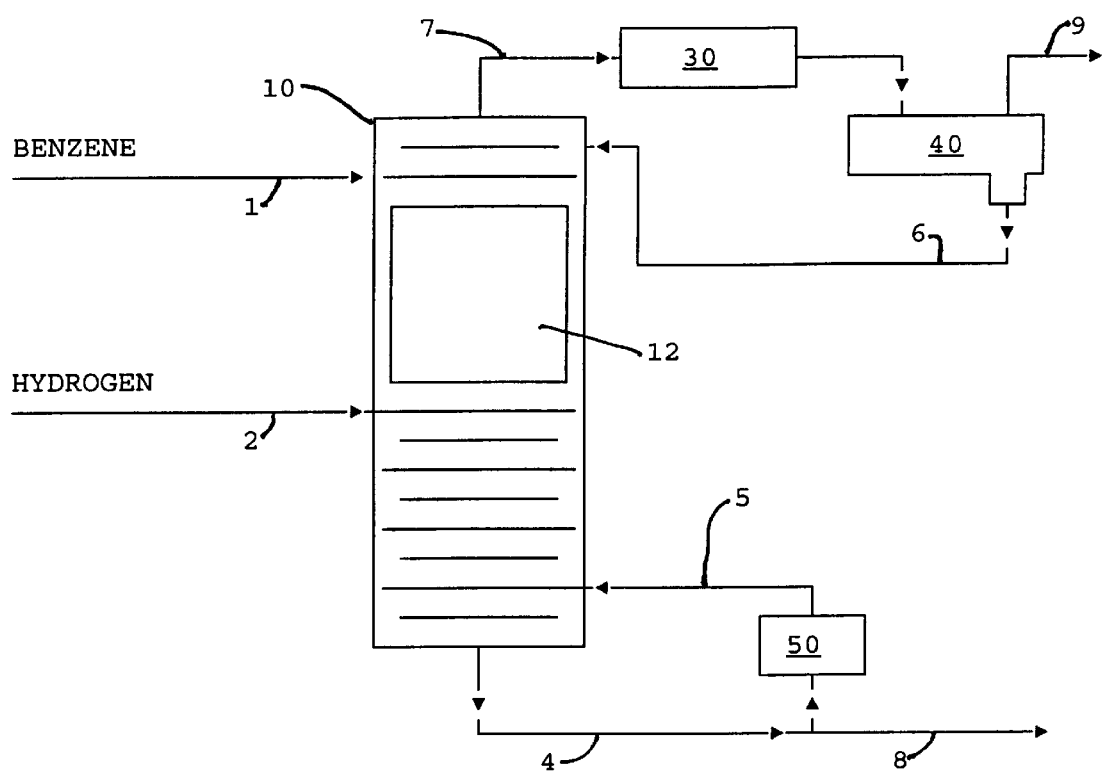

HYDROGENATION OF BENZENE TO CYCLOHEXANE

BACKGROUND OF THE INVENTION

1. Field of the Invention

The present invention relates to the hydrogenation of benzene to produce cyclohexane. More particularly the invention relates to a process wherein the hydrogenation of the benzene and separation of the product by distillation is carried out simultaneously in a distillation column reactor.

2. Related Information

Cyclohexane is the main precursor for the production of nylon products and as such the demand remains strong. Cyclohexane was first obtained by the direct fractional distillation of suitable crude petroleum refinery streams. Now the major portion of cyclohexane is obtained from the direct hydrogenation of benzene. Conventionally the reaction is carried out in vapor or mixed phase using a fixed bed reaction. The reactor temperature is controlled to be between 350 to 500° F. Higher temperatures can lead to thermodynamic limitations on benzene conversion, thermal cracking and increased by-product.

Peterson in U.S. Pat. No. 2,373,501 discloses a liquid phase process for the hydrogenation of benzene to cyclohexane wherein a temperature differential is maintained between the top of the catalyst bed where benzene is fed and the outlet where substantially pure cyclohexane is withdrawn. The temperature differential is due to the change in the exothermic heat of reaction released as less and less benzene is converted as the concentration of benzene decreases. Specifically the top of the catalyst bed is at a higher temperature than the lower catalyst bed. Hydrogen is supplied counter current to the benzene/cyclohexane flow. Temperature control coils are disposed within the reactor to maintain the temperature differential if the exothermic heat of reaction is not sufficient or to cool the bed if too much heat is released. Peterson recognizes that although the bulk of his reaction takes place in the liquid phase a portion of the benzene and cyclohexane will be vaporized, especially near the top of the reactor where the benzene concentration is highest and conversion is highest. A reflux condenser is provided to condense the condensible material and return it to the reactor. Thus, a substantial portion of the heat of reaction is removed by condensation of the reactants vaporized throughout the reaction. Peterson maintains a liquid level above the topmost catalyst bed but allows room for vapors to escape to the condenser where the heat of reaction is removed.

Larkin, et al. in U.S. Pat. No. 5,189,233 disclose another liquid phase process for the hydrogenation of benzene to cyclohexane. However, Larkin, et al utilize high pressure (2500 psig) to maintain the reactants in the liquid state. In addition Larkin, et al disclose the use of progressively more active catalyst as the concentration of benzene decreases to control the temperature and unwanted side reactions.

Hui, et al. in U.S. Pat. No. 4,731,496 disclose a gas phase process for the hydrogenation of benzene to cyclohexane over a specific catalyst. The catalyst reported therein is nickel supported on a mixture of titanium dioxide and zirconium dioxide.

The hydrogenation of benzene is also useful to remove that aromatic compound from gasoline streams. One example of this process is disclosed by Hsieh, et al in U.S. Pat. No. 5,210,348 wherein hydrogenation of the benzene fraction is used alone or in combination with alkylation. The hydrogenation of the benzene is disclosed to be in a standard single pass fixed bed reactor. In some schemes for the reduction of aromatic compounds in gasoline the ASTM D-86 90% point is specified such that the aromatic and unsaturated cyclic and polycyclic compounds are precluded from the gasoline blending pool. This has been termed a T-90 gasoline stock having a desired ASTM 90% point. The resultant T-90+ bottoms which are largely unsaturated cyclic and polycyclic compounds must be disposed of and hydrogenating them to produce lighter more saturated compounds for the gasoline pool is an attractive alternative.

A typical problem with the hydrogenation of benzene to cyclohexane is the competing reactions. Particularly isomerization to methyl cyclopentane is unwanted. Additionally at higher temperatures cracking of the ring occurs producing undesirable $C_5$ and lighter products. U.S. Pat. No. 5,773,670 discloses a process wherein unsaturated cyclic and polycyclic compounds (particularly benzene) are hydrogenated. In the process disclosed therein the hydrogen and unsaturated cyclic and polycyclic compounds are fed together as one stream below the catalyst bed in the distillation column reactor. In addition, to achieve complete conversion of the benzene to cyclohexane a polishing reactor was necessitated.

U.S Pat. No. 5,856,602 discloses the hydrogenation of a selected aromatic compound contained in a naphtha stream by feeding the naphtha stream and hydrogen to a distillation column reactor below the bed containing the catalyst.

It has been found that a downflow catalytic distillation reactor, that is, one in which the benzene containing stream is fed above the catalyst zone provides very high conversion. The major by product in conventional reactions is methyl cyclopentane, which is not present in the present reaction.

SUMMARY OF THE INVENTION

The present invention comprises feeding benzene to a distillation column reactor at a point above the catalyst bed and a hydrogen stream at an effectuating hydrogen partial pressure of at least about 0.1 psia to less than 200 psia, preferably less than 170 psia in the range of 75 to 150 psia to the distillation column reactor at a point below the bed containing a hydrogenation catalyst which is a component of a distillation structure and hydrogenating substantially all of the benzene.

The hydrogen rate must be adjusted such that it is sufficient to support the hydrogenation reaction and replace hydrogen lost from the catalyst but kept below that which results in flooding of the column which is understood to be the "effectuating amount of hydrogen" as that term is used herein. Generally the mole ratio of hydrogen to benzene in the feed to the fixed bed of the present invention will be about 3:1 to 15:1, preferably up to about 10:1.

The term "reactive distillation" is used to describe the concurrent reaction and fractionation in a column. For the purposes of the present invention, the term "catalytic distillation" includes reactive distillation and any other process of concurrent reaction and fractional distillation in a column regardless of the designation applied thereto.

BRIEF DESCRIPTION OF THE DRAWING

The FIGURE is a flow diagram of one embodiment of the invention.

DETAILED DESCRIPTION OF THE INVENTION

To provide the desired degree of temperature and residence time control a process and apparatus is provided wherein the reaction liquid is boiling within a distillation column reactor. Overheads are withdrawn and condensed with some of the condensate being returned to the distillation column reactor as reflux. The advantage of the present process is that due to the continual reflux a portion of the benzene is always condensing on the catalyst structure.

The present hydrogenation may be carried out to produce substantially pure cyclohexane from benzene.

The hydrogenation described herein is an exothermic reaction. In the past the temperature has been controlled by quench at strategic points within a reactor by addition of cool hydrogen. The addition of the hydrogen also acted to maintain a molar excess of hydrogen within the reactor to prevent coking and other undesirable side reactions. It is believed that in the present reaction catalytic distillation is a benefit, because all the components are boiling, whereby the temperature of reaction is controlled by the boiling point of the mixture at the system pressure and the reaction and distillation are occurring concurrently in the same reaction distillation column. The heat of reaction simply creates more boil up, but no increase in temperature at a given pressure.

The present invention carries out the method in a catalyst packed column which can be appreciated to contain a vapor phase and some liquid phase as in any distillation. The distillation column reactor is operated at a pressure such that the reaction mixture is boiling in the bed of catalyst. The present process for hydrogenating benzene operates at overhead pressure of said distillation column reactor in the range between 0 and 350 psig, preferably 200 or less, such as 75 to 200 psig and temperatures in said distillation reaction bottoms zone in the range of 100 to 500° F., preferably 280 to 380° F. The feed weight hourly space velocity (WHSV), which is herein understood to mean the unit weight of feed per hour entering the reaction distillation column per unit weight of catalyst in the catalytic distillation structures, may vary over a very wide range within the other condition perimeters, e.g. 0.1 to 35.

In the current process the temperature is controlled by operating the reactor at a given pressure to allow partial vaporization of the reaction mixture. The exothermic heat of reaction is thus dissipated by the latent heat of vaporization of the mixture. The vaporized portion is taken as overheads and the condensible material condensed and returned to the column as reflux.

Without limiting the scope of the invention it is proposed that the mechanism that produces the effectiveness of the present process is the condensation of a portion of the vapors in the reaction system, which occludes sufficient hydrogen in the condensed liquid to obtain the requisite intimate contact between the hydrogen and the benzene in the presence of the catalyst to result in their hydrogenation. Additionally, the vaporization of the liquid feed removes a substantial amount of the exothermic heat of reaction. Since the liquid is at the boiling point in the reactor, the temperature may be controlled by the pressure. An increase in pressure increases the temperature and a decrease in pressure decreases the temperature.

The downward flowing liquid causes additional condensation within the reactor as is normal in any distillation. The contact of the condensing liquid within the column provides excellent mass transfer for dissolving the hydrogen within the reaction liquid and concurrent transfer of the reaction mixture to the catalytic sites. It is thought that this condensing mode of operation results in the excellent conversion and selectivity of the instant process and allows operation at the lower hydrogen partial pressures and reactor temperatures noted. A further benefit that this reaction may gain from catalytic distillation is the washing effect that the internal reflux provides to the catalyst thereby reducing polymer build up and coking. Internal reflux may vary over the range of 0.2 to 20 L/D (wt. liquid just below the catalyst bed/wt. distillate) give excellent results.

A preferred embodiment is for the production of cyclohexane from the hydrogenation of benzene. When cyclohexane is the product, the benzene containing feed is characterized as preferably containing at least 5 wt % benzene up to 100 wt %. Other components are typically $C_5$, $C_6$ and $C_7$ hydrocarbons. Since other unsaturated compounds may be hydrogenated, the presence of these compounds are detrimental to the process when cyclohexane is the desire product. Preferably other unsaturated compounds should be limited to less than 30% of the feed. Cyclohexane is the preferred diluent, since it is the desired product. However, other inerts such as other alkanes are acceptable, such as $C_5$'s Up to $C_9$'s.

The present process is also quite well suited for removing the benzene from reformate streams, so that they may be used as gasoline blending stock, by selective hydrogenation. The operation of the distillation column reactor to maintain a desired aromatic fraction in the reaction action zone is described in U.S. Pat. No. 5,856,602, which is incorporated herein in its entirety.

As described the catalytic material employed in the hydrogenation process is in a form to serve as distillation packing. Broadly stated, the catalytic material is a component of a distillation system functioning as both a catalyst and distillation packing, i.e., a packing for a distillation column having both a distillation function and a catalytic function.

The reaction system can be described as heterogenous since the catalyst remains a distinct entity. Any suitable hydrogenation catalyst may be used, for example Group VIII metals of the Periodic Table of Elements as the principal catalytic component, alone or with promoters and modifiers such as palladium/gold, palladium/silver, cobalt/zirconium, nickel preferably deposited on a support such as alumina, fire brick, pumice, carbon, silica, resin or the like.

Among the metals known to catalyze the hydrogenation reaction are platinum, rhenium, cobalt, molybdenum, nickel, tungsten and palladium. Generally, commercial forms of catalyst use supported oxides of these metals. The oxide is reduced to the active form either prior to use with a reducing agent or during use by the hydrogen in the feed. These metals also catalyze other reactions, most notably dehydrogenation at elevated temperatures. Additionally they can promote the reaction of olefinic compounds with themselves or other olefins to produce dimers or oligomers as residence time is increased.

The catalyst may be prepared in the form of a catalytic distillation structure. More particularly the hydrogenation catalyst is generally a metal supported on an alumina carrier in the form of extrudates or spheres. The extrudates or spheres are placed in porous containers and suitably supported in the distillation column reactor to allow vapor flow through the bed, yet provide a sufficient surface area for catalytic contact.

The catalyst component may take several forms. In the case of particulate catalytic material, generally from 60 mm to about 1 mm down through powders, is enclosed in a porous container such as screen wire, or polymeric mesh. The material used to make the container must be inert to the reactants and conditions in the reaction system. The screen wire may be aluminum, steel, stainless steel, and the like. The polymer mesh may be nylon, Teflon, or the like. The mesh or threads per inch of the material used to make the container is such that the catalyst is retained therein and will not pass through the openings in the material. Although the catalyst particles of about 0.15 mm size or powders may be used and particles up to about ¼ inch diameter may be employed in the containers.

A preferred catalyst structure for the hydrogenation of benzene comprises at least one plurality of flexible, semi-rigid open mesh tubular elements filled with a particulate catalytic material (catalyst component) and sealed at both ends, intimately associated with and supported by a wire mesh screen coiled into a spiral having a longitudinal axis, said tubular element being arrayed at an angle to the longitudinal axis thereby forming a bale and is described in detail in U.S. Pat. 5,431,890. The flexible, semi-rigid open mesh tubular element filed with a particulate catalytic material preferably has a fastener every 1–12 inches along the length of the tube to form a multiple link shaped catalytic distillation structure. The links formed by the fasteners may be evenly or irregularly spaced.

Bale shaped catalytic distillation structures are formed by placing at least one tubular element on top of the wire mesh screen, such as demister wire, in a diagonal array, such that when the wire mesh screen is rolled up, the rolled structure provides a new and improved catalytic distillation structure. Further embodiments include multiple stack arrangements of alternating wire screen mesh and tubular elements that are rolled into a new bale shaped catalytic distillation structure. The tubular elements on alternating layers are preferably arrayed on the wire mesh screen in opposite directions such that their paths cross. Each tubular element will define a spiral within the bale.

A most preferred catalyst structure for the hydrogenation is described in U.S. Pat. No. 5,730,843. Disclosed therein is a contact structure, useful as a distillation structure which has a rigid frame made of two substantially vertical duplicate grids spaced apart and held rigid by a plurality of substantially horizontal rigid members and a plurality of substantially horizontal wire mesh tubes mounted to the grids to form a plurality of fluid pathways among the tubes. At least a portion of the wire mesh tubes contain a particulate catalytic material. The catalyst within the tubes provides a reaction zone where catalytic reactions may occur and the wire mesh provides mass transfer surfaces to effect a fractional distillation. The spacing elements provide for a variation of the catalyst density and loading and structural integrity.

Referring now to the FIGURE there is shown a flow diagram showing the hydrogenation of benzene. Benzene is fed via line 1 at a point above the catalyst bed 12 and hydrogen via line 2 at a point below the catalyst bed 12 contained in distillation column reactor 10. If desired the benzene feed may be diluted with cyclohexane. Heat necessary for start up and to balance the process is provided by circulating the bottoms stream 4 through reboiler 50 and return line 5. The benzene flows downward into the bed where a portion reacts with the rising hydrogen to form a reaction mixture containing the reaction product cyclohexane, unreacted benzene and unreacted hydrogen. The exothermic heat of reaction causes more boil up of the reaction mixture with the vaporized portion leaving the column as overheads via flow line 7. Unreacted hydrogen also exits with the overheads. The gaseous overheads containing unreacted benzene, cyclohexane, lighter compounds and hydrogen are passed through condenser 30 where substantially all of the benzene and cyclohexane are condensed. The overheads stream is then passed to receiver/separator 40 where the gas which is mostly hydrogen is separated and the liquid collected. The gas is removed via line 9 for recycle or use later in the process.

All of the condensed liquid is returned to the distillation column as reflux via flow line 6 where it provides additional cooling and condensing within the column. The bottoms, containing a small amount of benzene and cyclohexane, are removed via flow line 4 with a portion being recirculated through reboiler 50 and flow line 5. There is no overheads liquids product taken. All of the product is taken as bottoms via flow line 8.

The present process allows for the use of much lower hydrogen partial pressures and somewhat lower temperatures than earlier processes to obtain the same results of about 100% benzene conversion with 100% selectivity to cyclohexane.

EXAMPLE 1

A three inch diameter distillation column reactor was used. The rigid catalyst structure was filled with 6.77 pounds of Crosfield HTC-400 catalyst (12% nickel on alumina) as described above and placed in the middle 9 feet of the reactor in the packing as described in U.S. Pat. No. 5,730,843. The bottom 50 feet were filled with inert distillation packing.

Typical Conditions and results are shown in Table I below.

TABLE I

| | | | |
|---|---|---|---|
| Time on stream, hrs | 134 | 254 | 314 |
| Pressure, psig | 200 | 200 | 200 |
| Reaction Temp., ° F. | | | |
| Top Cat. Bed | 367 | 381 | 383 |
| Btm. Cat. Bed | 351 | 349 | 346 |
| Internal Reflux Ratio (L/F) | 23.6 | 19.1 | 15.5 |
| Feed Rate, lbs/hr liq. | 3.1 | 6.0 | 8.1 |
| H2 Rate scfh, gas | 151 | 151 | 151 |
| H2/Bz mole ratio | 9.9 | 5.2 | 3.8 |
| Benzene in feed, wt % | 99.93 | 99.93 | 99.93 |
| H2 pp, psia | 75.5 | 77.6 | 79.9 |
| Benzene in btms., wt. | 8 ppm | <250 ppm | 6.1% |
| Bottoms analysis, wt % Cyclohexane | 99.9 | 99.6 | 93.1 |

The invention claimed is:

1. In a process for the production of cyclohexane by the hydrogenation of benzene comprising the steps of:
   (a) feeding a first stream comprising benzene to a distillation column reactor containing a bed of hydrogenation catalyst;
   (b) feeding a second stream comprising hydrogen to said distillation column reactor at a point below said bed;
   (c) contacting the benzene and hydrogen at a hydrogen partial pressure of from 0.1 to 200 psia, in the presence of a hydrogenation catalyst thereby reacting a portion of the benzene with a portion of the hydrogen to form a reaction mixture containing cyclohexane and, unreacted hydrogen and unreacted benzene;
   (d) maintaining the pressure in the distillation column reactor such that a portion of the reaction mixture is boiling;
   (e) removing gaseous overheads, components from the reaction mixture and hydrogen from the distillation column reactor;
   (f) condensing a portion of the overheads from the distillation column reactor; and (g) returning a portion of the condensed overheads to the distillation column reactor as reflux, wherein the improvement comprises feeding said first stream at a point above said bed of hydrogenation catalyst.

2. The process according to claim 1 wherein the overhead pressure of the distillation column reactor is between 0 and 350 psig.

3. The process according to claim 1 wherein the hydrogen partial pressure is between 0.1 and 170 psia.

4. The process according to claim 3 wherein the hydrogen partial pressure is between 75 and 150 psia.

5. The process according to claim 1 wherein the overhead pressure of the distillation column reactor is between 0 and 350 psig.

6. The process according to claim 1 wherein the total pressure is about 200 psig, the reaction temperature in said bed is about 346–383° F. and over 90% of the benzene is reacted with hydrogen to form cyclohexane.

7. The process according to claim 1 wherein the mole ratio of hydrogen to benzene feed is about 3.0 to 15.0:1.

8. The process according to claim 1 wherein said overheads comprise benzene, cyclohexane and hydrogen and all of the overheads benzene and cyclohexane is condensed and returned to the distillation column reactor as reflux.

9. The process according to claim 8 wherein a liquid bottoms product comprising benzene and cyclohexane is withdrawn from the distillation column reactor.

10. In a process for the production of cyclohexane from the hydrogenation of benzene comprising the steps of:

(a) feeding a first stream comprising benzene to a distillation column reactor containing a bed of hydrogenation catalyst;

(b) feeding a second stream containing hydrogen to said distillation column reactor at a point below said bed, said hydrogen being at a mole ratio to benzene of between 3.0 and 10.0;

(c) contacting the benzene and hydrogen at a total overhead pressure in the range of about 75 to 200 psig, a hydrogen partial pressure in the range of 75 to 150 psia and a reaction temperature of between 280–380° F., in the presence of a hydrogenation catalyst prepared in the form of a catalytic distillation structure thereby reacting substantially all of the benzene with a portion of the hydrogen to form a reaction mixture containing cyclohexane and unreacted hydrogen;

(d) maintaining the pressure in the distillation column reactor such that a portion of the reaction mixture is boiling at the temperature of reaction in said bed;

(e) removing gaseous benzene, cyclohexane and hydrogen as overheads from the distillation column reactor;

(f) condensing substantially all of the benzene and cyclohexane removed as overheads from the distillation column reactor;

(g) returning a substantially all of the condensed benzene and cyclohexane to the distillation column reactor as reflux; and (h) withdrawing a bottoms liquid product containing cyclohexane from the distillation column, wherein the improvement comprises feeding said first stream at a point above said bed of hydrogenation catalyst.

* * * * *